(12) United States Patent
Horiguchi

(10) Patent No.: US 7,821,764 B2
(45) Date of Patent: Oct. 26, 2010

(54) VOLTAGE CONVERTER

(76) Inventor: Noboru Horiguchi, 1518-5, Oaza Higashibun, Utazu-cho, Ayauta-gun, Kagawa (JP) 7690213

( * ) Notice: Subject to any disclaimer, the term of this patent is extended or adjusted under 35 U.S.C. 154(b) by 385 days.

(21) Appl. No.: 11/989,592

(22) PCT Filed: Jul. 28, 2006

(86) PCT No.: PCT/JP2006/315445
§ 371 (c)(1),
(2), (4) Date: Jan. 29, 2008

(87) PCT Pub. No.: WO2007/015555
PCT Pub. Date: Feb. 8, 2007

(65) Prior Publication Data
US 2009/0091873 A1    Apr. 9, 2009

(30) Foreign Application Priority Data
Aug. 1, 2005    (JP)    ............... 2005-222871

(51) Int. Cl.
*H01T 23/00* (2006.01)
(52) U.S. Cl. .................................. 361/230
(58) Field of Classification Search ............... 361/230, 361/231
See application file for complete search history.

(56) References Cited

U.S. PATENT DOCUMENTS

| | | | | |
|---|---|---|---|---|
| 2,089,555 A | * | 8/1937 | Hull et al. | 315/52 |
| 2,156,156 A | * | 4/1939 | Mahlck | 205/766 |
| 2,400,456 A | * | 5/1946 | Haine et al. | 331/127 |
| 3,465,190 A | * | 9/1969 | Betoule et al. | 313/105 R |
| 3,846,300 A | * | 11/1974 | Inoue | 210/717 |
| 4,090,448 A | * | 5/1978 | Rose et al. | 102/210 |
| 5,909,086 A | * | 6/1999 | Kim et al. | 315/111.21 |
| 6,267,864 B1 | * | 7/2001 | Yadav et al. | 205/341 |
| 7,056,454 B2 | * | 6/2006 | Fujino | 252/520.2 |
| 2004/0071629 A1 | | 4/2004 | Nakaya et al. | |
| 2005/0052824 A1 | * | 3/2005 | Jyoya et al. | 361/321.5 |
| 2005/0234524 A1 | * | 10/2005 | Horiguchi et al. | 607/50 |

FOREIGN PATENT DOCUMENTS

| | | |
|---|---|---|
| EP | 1 128 404 A | 8/2001 |
| JP | 2003 059622 | 2/2003 |
| JP | 2003 139342 | 5/2003 |
| JP | 2004 351299 | 12/2004 |
| JP | 2005 046771 A | 2/2005 |

* cited by examiner

*Primary Examiner*—Ronald W Leja
(74) *Attorney, Agent, or Firm*—Bacon & Thomas, PLLC

(57) ABSTRACT

A voltage converter having a sealed case, a pair of opposing, spaced apart planar electrodes located within the sealed case, a pack of porous dielectric powder filled between the planar electrodes, and an auxiliary electrode electrically connected to one of the planar electrodes and having a portion extending through the pack of porous dielectric powder toward the other planar electrode. When a DC high voltage is applied to one of the planar electrodes, a DC source voltage containing a specific pulsating component is outputted from the other planar electrode.

12 Claims, 23 Drawing Sheets

VOLTAGE CONVERTER

TECHNICAL FIELD

The present invention relates to a voltage converter for generating an apply voltage suitable for driving a discharging or charging device for a negative ion generating device or an electric potential treatment instrument for applying negative ions.

BACKGROUND ART

Atmospheric ion is a collective term for fine particles that are electrically charged positively or negatively and suspended in the atmosphere. Of those, particles that carry a positive charge are called positive ions and particles that carry a negative charge are called negative ions.

Atmospheric ions are generated when gas molecules in the atmosphere are ionized. When particles in the atmosphere mainly composed of nitrogen molecules and oxygen molecules are given energy equivalent to their ionization energy, the particles release electrons and become initial positive ions. The released electrons react with other atmospheric particles to form initial negative ions.

These initial ions react with minor components of the atmosphere and assemble into nuclear ions. The nuclear ions further react with components of the atmosphere and bind to water molecules to form cluster ions.

A device which can artificially generate cluster ions readily and effectively is a negative ion generating device brought up herein.

In general, negative ion generating devices are largely divided into four types based on the way of generating ions; Leonard type, corona discharge type, electron emission type, and radioactive material type.

All the types have advantages and disadvantages. Among them, corona discharge type negative ion generating devices, which generate ions by forcibly applying a flow of oxygen molecules to electrons moving from one electrode to another using the ionizing effect of corona discharge, can be relatively compact and produced at low costs and can continuously generate a large amount of negative ions. Therefore, corona discharge type negative ion generating devices are used widely on its own or in combination with electric potential treatment instruments, health appliances, air purification systems, air conditioners and so on.

Electrons emission type negative ion generating devices generate negative ions of oxygen by supplying electrons generated by a discharge to oxygen molecules in the air. This type of ion generators has generally the same characteristics as the corona discharge type ion generators.

The corona discharge type and electron emission type negative ion generating devices are generally the same in that they have a discharging electrode and a high-voltage DC power source, and a negative high voltage (−3 to −9 KV, for example) from the high-voltage DC power source is applied to the discharging electrode and ionization by corona discharge is induced to generate negative ions although there is a slight difference in the structure of the electrode (see JP-A-2003-139342 (pp. 1 to 9 of the specification and FIGS. 1 to 5) and JP-A-2001-56395 (pp. 1 to 5 of the specification and FIGS. 1 to 9), for example).

The problems of such discharge type negative ion generating devices are how efficiently stable negative ions can be generated and how effectively the generated negative ions can be applied to a human body or the like. One method for improving the negative ion generation efficiency is to apply a driving voltage to the discharging electrode intermittently (see JP-A-2003-59622 (pp. 1 to 10 of the specification and FIGS. 1 to 31), for example).

Also, some electric potential treatment instruments and cosmetic or health appliances using negative ions have a charging means for charging a human body to a positive potential (or ground potential) in order to apply generated negative ions to the human body effectively.

To apply the generated negative ions intensively to a target such as human body with a charging means or the like produces high treatment effect and high heath promotion effect and has good practical use. However, such a charging means cannot be used in a negative ion generating device for releasing negative ions into indoor air used on its own or incorporated in an air purification system or air conditioner.

Thus, it is important to improve the negative ions generation efficiency itself. To improve the negative ion generation efficiency of a negative ion generating device leads to improvement of the negative ions concentration effect of the charging means.

In reality, however, the negative ion generation efficiency cannot be necessarily improved by driving a charging means intermittently with an intermittent drive means. On the contrary, such a charging means makes the control circuit on the power source side complex and results in an increase in production costs.

SUMMARY OF THE INVENTION

The present inventor has developed a voltage converter with specific RC characteristics having first and second electrodes opposed to each other in a nonconductive sealed case and porous inorganic powder filled in the space between the first and second electrodes and maintained at a prescribed humidity level, and has succeeded in improving the negative ion generation efficiency effectively by applying a negative high voltage from a DC high-voltage power source to a discharging electrode for generating negative ions via the voltage converter (see JP-A-2004-355896 (pp. 1 to 11 of the specification and FIGS. 1 to 20) and JP-A-2005-296441 (pp. 1 to 11 of the specification and FIGS. 1 to 14).

In the above configuration, an RC oscillation circuit effect is generated by a resistance component and a capacitance component generated by the conductive function derived from the water retention function of the porous inorganic powder with high moisture retention properties and the dielectric function of a multiplicity of air holes and gaps in and between the porous inorganic powder particles, and an effective pulsating voltage generation effect is thereby obtained. As a result, corona discharge is generated with high efficiency and a large amount of negative ions can be generated.

In addition, the values of R and C can be controlled relatively easily by adjusting the humidity. Also, since porous inorganic powder is filled in the space between the electrodes, the voltage converter has very high dielectric strength and exhibits stable performance even under a very high voltage conditions.

To generate a large amount of negative ions at the discharging electrode with high efficiency, it is necessary to generate stable corona discharge continuously at the discharging electrode.

To do so, the structure of the discharging electrode is important, and the discharging apply voltage applied to the discharging electrode is as important as it.

The discharging apply voltage is preferably a pulsating voltage with a specific period. The pulsating voltage generation performance depends on the performance of the voltage converter.

As a result of studies conducted from this viewpoint, the devices developed and proposed by the present inventor and disclosed in JP-A-2004-355896 and JP-A-2005-296441 have been found to be the most effective. However, the devices still have room for improvement in their absolute capacitance.

The present invention has been made to overcome the problem, and it is, therefore, an object of the present invention to provide a voltage converter with simple structure and high electrostatic capacitance by modifying the structure of the first and second electrodes of the voltage converter.

In accomplishing the foregoing object, there is provided in accordance with one aspect of the present invention a voltage converter, having a sealed case, a pair of first and second planar electrodes located in the sealed case and opposed to each other with a gap therebetween, a pack of porous dielectric powder filled in the gap, and a first auxiliary electrode electrically connected to the first planar electrode and having a portion extending in the pack of porous dielectric powder toward the second planar electrode, whereby when a DC high voltage is applied to one of the first and second planar electrodes, a DC source voltage containing a specific pulsating component is outputted from the other one of the first and second planar electrodes.

When an auxiliary electrode electrically connected to the first planar electrode and having a portion extending in the pack of porous dielectric powder toward the second planar electrode is provided between the first and second planar electrodes opposed to each other as described above, the auxiliary electrode creates substantially the same effects as increasing the areas of the first and second planar electrodes opposed to each other as a whole and as decreasing the distance between the first and second planar electrodes.

Even when the auxiliary electrode is provided, the dielectric constant of the porous dielectric powder does not change. Therefore, the electrostatic capacitance of the voltage converter as a capacitive voltage converter significantly increases. When the electrostatic capacitance increases, the amplitude of the pulsating voltage to be applied to a discharging electrode for generating negative ions increases and corona discharge occurs more easily. As a result, the negative ion generation efficiency increases.

In another aspect, the present invention provides a negative ion generating device, comprising the above voltage converter, a DC high-voltage power source electrically connected to the first planar electrode, and a discharging electrode having an input connected to the DC source voltage which contains a specific pulsating component and which is outputted from the voltage converter.

BRIEF DESCRIPTION OF THE DRAWINGS

Other objects, features and advantages of the present invention will become apparent from the detailed description of the preferred embodiments of the invention which follows, when considered in the light of the accompanying drawings, in which.

DETAILED DESCRIPTION OF THE PREFERRED EMBODIMENTS OF THE INVENTION

First Embodiment

FIGS. 1 to 7 illustrate the configuration and function of a voltage converter according the present invention applied to a negative ion generating device for an electric potential treatment instrument as a first embodiment of the present invention.

Figure 1:
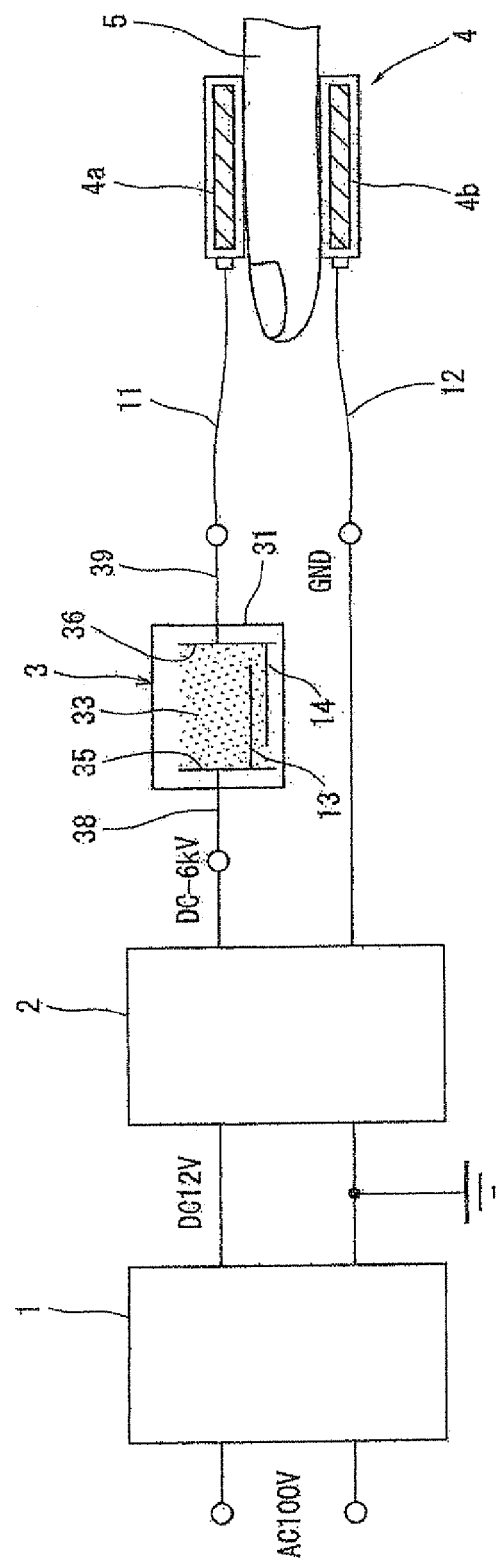
FIG. 1 is a block diagram illustrating the configuration of a negative ion generating device for an electric potential treatment instrument according to a first embodiment to which a voltage converter of the present invention is applied.

FIG. 1 illustrates the general configuration of the negative ion generating device for an electric potential treatment instrument. Designated as 1 is an AC adapter (AC/DC converter) as an AC/DC conversion means constituted of a rectifier for converting an AC supply voltage of 100 V supplied from a commercial AC power source into a DC voltage of +12 V and a transformer, as 2 is a DC high-voltage power source unit (which will be hereinafter referred to simply as DC high-voltage power source) as a boosting means for boosting the DC voltage of +12 V to a negative high voltage of –6 KV, as 3 is a voltage converter for converting the DC supply voltage from the DC high-voltage power source 2 into a DC supply voltage containing a specific pulsating component, and as 4 is a discharging section including discharging electrodes 4a and 4b and having an input connected to the voltage converter 3 for generating negative ions for electric potential treatment by means of the stable corona discharge with high efficiency.

The AC adapter 1 converts input power (AC 100V) received from, for example, a household AC power source 10 into a DC voltage of (+)12 V as described above. The DC high-voltage power source 2 boosts the DC voltage of (+)12 V outputted from the AC adapter 1 into a negative high voltage of about –6 KV by full-wave voltage doubling and inputs the negative high voltage of –6 KV into the voltage converter 3 through a DC negative voltage supply line. The voltage converter 3 converts the negative high voltage into a pulsating voltage with high peak values and desired stable frequency characteristics suitable to generate stable corona discharge efficiently (see FIG. 16(a) to FIG. 18(a)) and applies it to the discharging electrode 4.

Figure 2:
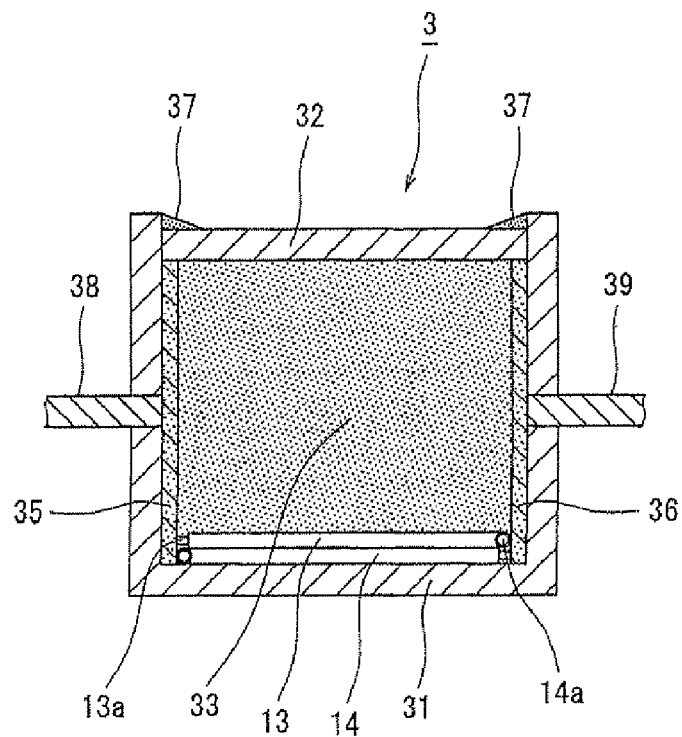
FIG. 2 is a vertical cross-sectional view of the voltage converter of the present invention as an essential component of the electric potential treatment instrument.
Figure 3:
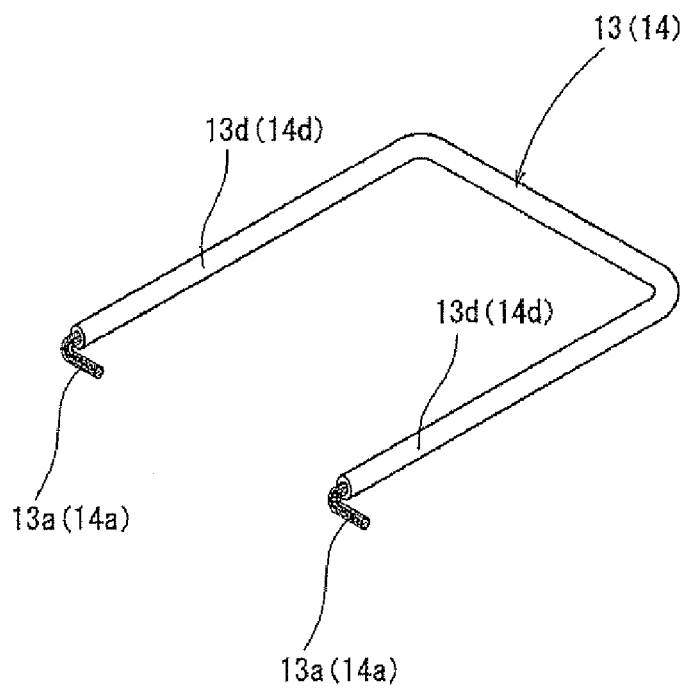
FIG. 3 is a perspective view illustrating the configuration of first and second auxiliary electrodes as essential components of the voltage converter.

As shown in FIGS. 2 and 3 in detail, the voltage converter 3 has a nonconductive case body 31 made of a synthetic resin such as ABS resin. The case body 31 is in the shape of a rectangular parallelepiped box with a bottom and an upper opening. A cap 32 is fitted in the upper opening of the case body 31. First and second planar electrodes 35 and 36 of a conductive metal (such as stainless steel or copper) are provided on inner opposite sides of the nonconductive case body 31. Designated as 13 is a U-shaped first auxiliary electrode 13 having leg portions 13d with first ends electrically connected to the first electrodes 35 and extending toward the second electrode 36. Provided also is a U-shaped second auxiliary electrode 14 having leg portions 14d with first ends electrically connected to the second electrodes 36 and extending toward the first electrode 36.

A pack of powder or particles of porous dielectric substance 33 (referred to as porous dielectric powder) is uniformly filled in the space in the nonconductive case body 31. The porous dielectric powder preferably has a particle diameter in the range of 0.1 μm to 1 mm, more preferably 1 μm to 500 μm, still more preferably 1 μm to 200 μm. The porous dielectric powder preferably has a dielectric constant of 2 to 10, more preferably 2.5 to 6. Examples of the porous dielectric powder include igneous rock powder, tuff powder, metal oxide powder and charcoal. Concrete examples of the porous dielectric powder include natural pumice powder, granite powder and charcoal powder.

The porous dielectric powder preferably has a water content of 1.5 to 8% by weight, more preferably 2 to 6% by weight, still more preferably 2.5 to 4.5% by weight.

The cap 32 is sealed hermetically with an adhesive (or a thermal sealing means) 37 to maintain the humidity in the case body 31 and the water content of the porous inorganic power at optimum levels. The relative humidity in the case body 31 is preferably maintained in the range of 45 to 75%, more preferably 50 to 70% at room temperature.

Figure 4:
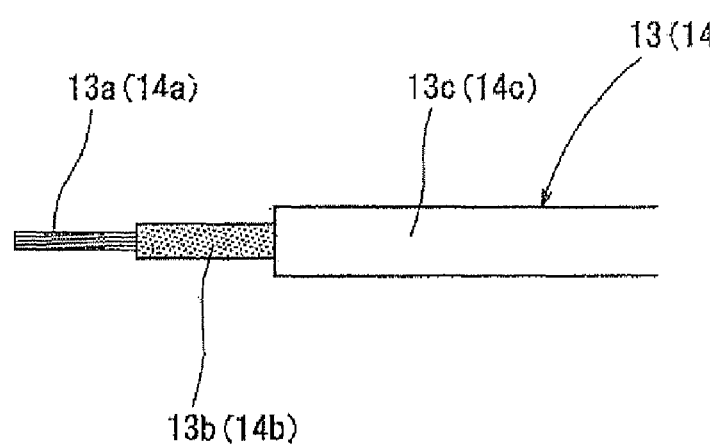
FIG. 4 is a view illustrating the structure of an insulating covered cable for the first and second auxiliary electrodes.

The first and second auxiliary electrodes 13 and 14 are made of insulating covered cables (high-voltage cables) having conductive cable cores 13a and 14a of tin-plated copper, insulating tubes 13b and 14b of an insulating material such as ilex, and exterior tubes 13c and 14c of an insulating material such as vinyl chloride, respectively, as shown in FIG. 3 and FIG. 4. The first and second auxiliary electrodes 13 and 14 are located at the bottom of the case body and stacked in part.

When the first and second auxiliary electrodes 13 and 14 electrically connected to the first and second planar electrodes 35 and 36 are provided between the first and second planar electrodes 35 and 36 opposed to each other as described above, the first and second auxiliary electrodes 13 and 14 can create substantially the same effects as increasing the areas of the first and second planar electrodes 35 opposed to each other and as decreasing the distance between the first and second planar electrodes 35 and 36.

As a result, the electrostatic capacitance of the voltage converter 3 as a capacitive voltage converter increases as described later.

Also, since the first and second auxiliary electrodes 13 and 14 are stacked in part, the auxiliary electrodes 13 and 14 are distributed generally uniformly in the space between the first and second planar electrodes and the electrostatic capacitance of the voltage converter 3 can be increased more effectively.

In addition, since the first and second auxiliary electrodes 13 and 14 are made of insulating covered cables, the first and second auxiliary electrodes 13 and 14 may be placed in contact with each other. Therefore, the first and second auxiliary electrodes 13 and 14 can be installed easily.

Moreover, since the first and second auxiliary electrodes 13 and 14 are located at the bottom of the case body 31 as shown in FIG. 2, when the case body 31 is filled with the porous dielectric powder 33 and sealed hermetically, the first and second auxiliary electrodes 13 and 14 can be easily fixed in the case body 31. Therefore, the first and second auxiliary electrodes 13 and 14 require any attaching or fastening means and thus can be produced easily.

The humidity in the case body 31 and water content of the porous dielectric powder 33 is desirably controlled to generate a discharging apply voltage (pulsating voltage) with desired frequency characteristics necessary to generate a stable corona discharge efficiently at the discharging electrode 4. Optimum humidity and water content may generally vary depending upon the kind of the porous dielectric powder 33 and can be determined by experiments.

The first planar electrode 35 of the voltage converter 3 for generating the pulsating voltage are connected to a −6 KV output terminal of the DC high-voltage power source 2 via a first lead terminal 38, and the second planar electrode 36 of the voltage converter 3 is connected to a first discharging electrode 4a, which will be described later, of the discharging electrode 4 via a second lead terminal 39.

When the impedance-frequency characteristics of the voltage converter 3 constituted as described above are measured, the impedance decreases along a gentle curve with increase of frequency. The conductance G is $1.6 \times 10^{-8}$ S ($=60$ MΩ) in a low-frequency range and increases exponentially with increase in frequency, and the capacitance C gradually decreases from a value around 15 PF and converges a value around 3 PF. The impedance of the voltage converter 3 has frequency characteristics derived from the properties of the porous dielectric powder 33 as a dielectric material between the first and second planar electrodes 35 and 36 and has a capacitance of a few PF. At the same time, the porous dielectric powder 33 filed in the space between the first and second planar electrodes 35 and 36 maintained at a high humidity of, for example, 62% at ambient temperature has conductivity caused by the water retained therein. That is, the voltage converter 3 has a resistance component R with a prescribed value and a capacitance component C with a prescribed capacitance derived from the porous dielectric powder 33, and the voltage converter 3 as a pulsating voltage generating unit is equivalent to an RC parallel oscillation circuit as shown in FIG. 5.

Figure 5:
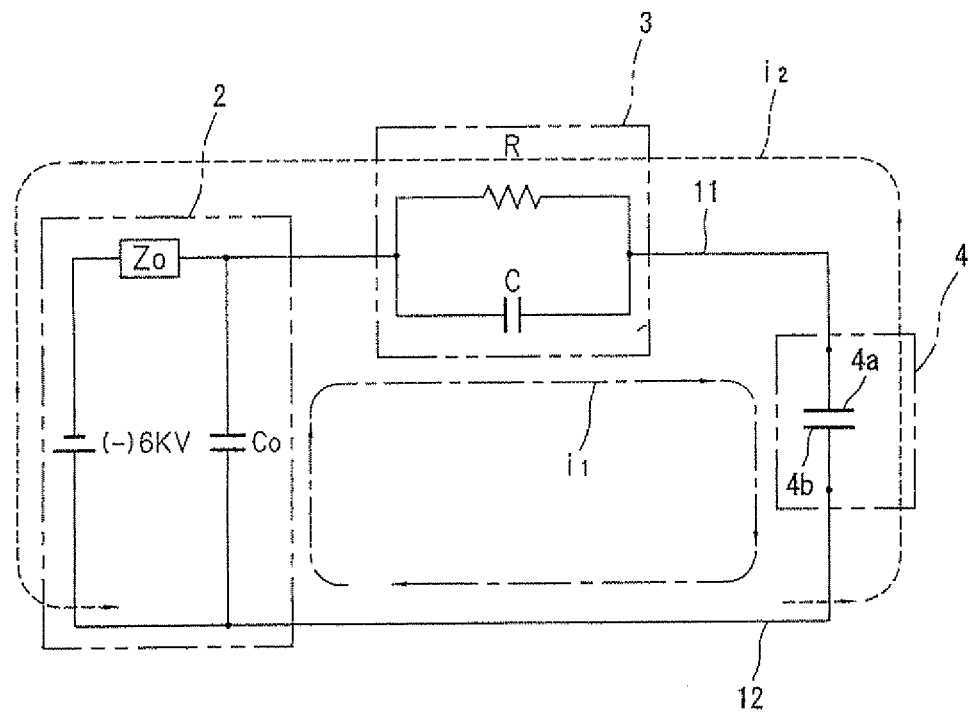
FIG. 5 is an equivalent circuit diagram illustrating the electrical configuration of the voltage converter.
Figure 6:
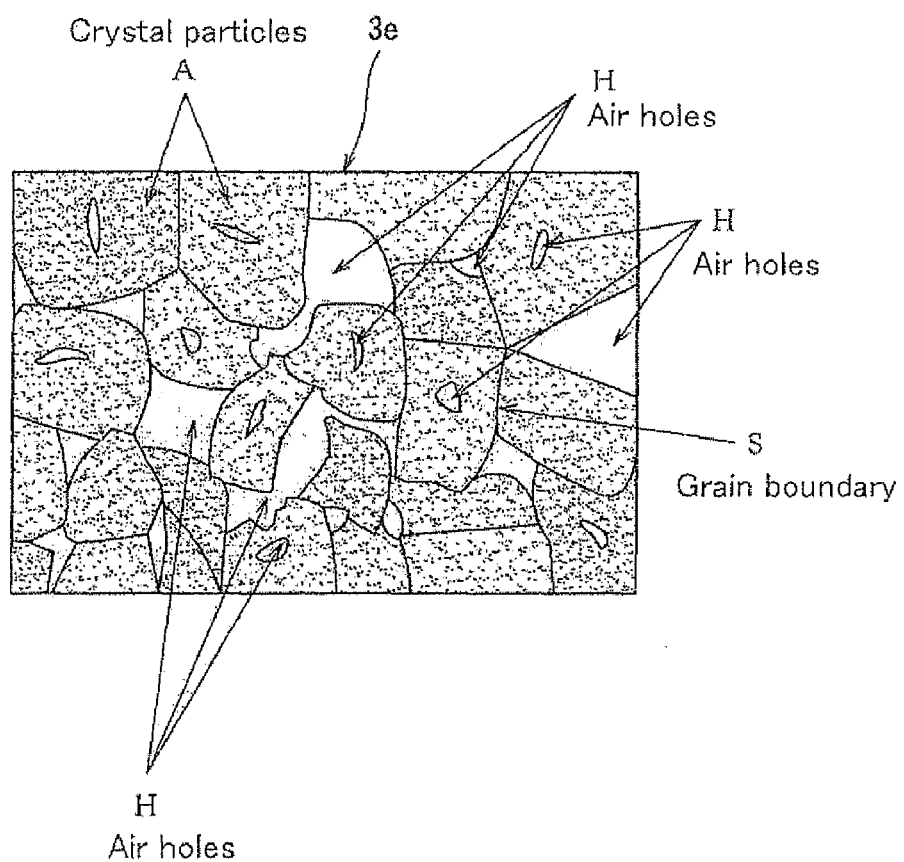
FIG. 6 is an image view illustrating the crystalline structure of porous dielectric powder in the voltage converter.

In FIG. 5, $C_0$ represents the internal capacitance of the DC power source, $Z_0$ represents the internal impedance of the DC power source, $i_1$ represents a corona discharge current, and $i_2$ represents a DC current flowing through the resistance component of the voltage converter 3. In the voltage converter 3, water is absorbed and retained in small air holes of a multiplicity of air holes H, H . . . among the particles of the porous dielectric powder 33 and small air holes in crystalline particles A, A . . . of the porous dielectric powder 33 as shown in FIG. 6 and creates a desired resistance component R in the pathway through which electricity flows. Therefore, a resistance necessary for an RC parallel oscillation circuit can be created. Also, the porous dielectric powder 33 under a high humidity condition functions as a desirable dielectric material and has a required capacitance C. As a result, an RC parallel oscillation circuit made up of a multiplicity of RC parallel circuit is formed between the first and second planar electrodes 35 and 36.

The DC voltage (−6 KV) from the DC high-voltage power source 2 is applied to the first planar electrode 35 via the resistance component R, and a high-frequency corona discharge current generated at the first and second planar electrodes 35 and 36 flows through a closed circuit including the capacitance $C_0$ in the power source and the capacitance C of the porous dielectric powder 33. Then, an effective pulsating voltage, as shown in FIG. 16(*a*), FIG. 17(*a*) and FIG. 18(*a*), which can be obtained by adding a prescribed vibration component (applying high-frequency modulation) to an input voltage from a DC high-voltage power source 2, which will be described later, can be obtained. As a result, corona discharge can be continuously generated at the discharging electrode 4 with high efficiency.

The results of experiments show that when the voltage to be applied to the first discharging electrode 4a of the discharging electrode 4 is converted into a pulsating voltage as described above, stable corona pulses are continuously discharged without being affected by the space charge around the first and second discharging electrodes 4a and 4b with high discharging efficiency and a large amount of negative ions are generated.

In general, stable corona pulses cannot be generated without a feedback circuit for a corona pulse current (a bypass capacitor is usually used). However, in the above configuration, at least one of a plurality of RC circuits combined serves as a feedback circuit for a corona pulse current and stable corona discharge is continuously generated.

Also, when a DC voltage of −6 KV is applied across the first and second planar electrodes 35 and 36 from the DC high-voltage power source 2, discharge occurs between the first and second planar electrodes 35 and 36. Then, electrons (e⁻) with negative charge produced by the discharge collide with the porous dielectric powder 33, and electrons bound in the crystalline particles A, A . . . of the porous dielectric powder 33 are released highly efficiently as free electrons and negative ions by the collision energy. The electrons and negative ions are gathered at the second planar electrode 36 through Brownian motion. This is considered to be the reason why a pulsating voltage with a specific period and an effective amplitude level is outputted from the output terminal of the second planar electrode 36.

The composition of a natural pumice stone powder as an example of the porous dielectric powder 33 which serves as both a dielectric material and a resistance is analyzed by fluorescent X-ray analysis. According to the result of the analysis, the natural pumice stone powder contains 44% (wt) of oxygen (O), 32% (wt) of silicon (Si), 9.8% (wt) of aluminum (Al), 3.8% (wt) of carbon, and 3.7% (wt) of iron. It also contains a small amount of calcium (Ca), potassium (K), sodium (Na), chloride (Cl), magnesium, (Mg) and so on.

When the structure inside the natural pumice stone is observed with a scanning electron microscope, there are many air holes H, H . . . (or voids) of various sizes in the crystalline particles A, A . . . as well as gaps between the crystalline particles A, A . . . (at the grain boundaries S, S, . . . between the particles).

In general metal materials, atoms are joined by metallic bonds in the crystal and the electrons in the outermost orbit of the atoms can move freely. Therefore, metals can conduct electricity well and has no capacitive component. In stone materials such as natural pumice stone, however, the atoms of main components such as oxygen, silicon, aluminum and carbon are joined by covalent bonds. Therefore, stone materials have much lower electric conductivity than metal materials. Also, a multiplicity of air holes (or voids) H, H . . . of various sizes in natural pumice stone each serve as a dielectric body and form one combined dielectric body, a specific capacitance is formed between the first and second planar electrodes 35 and 36 and the constituent atoms or ions can move relatively freely in the air holes by energy of the electric charge.

Figure 7:
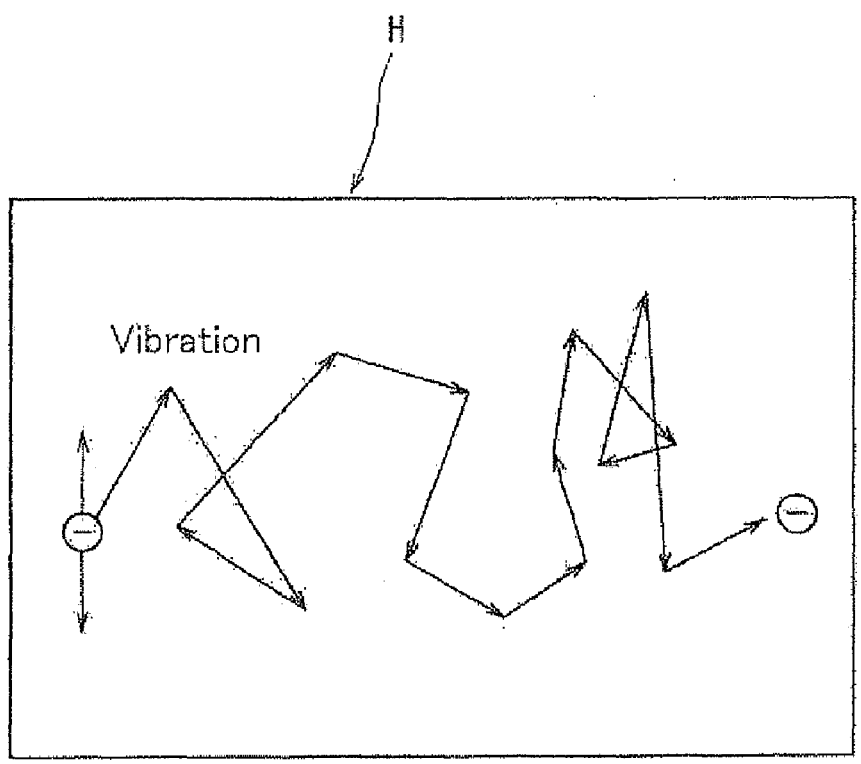
FIG. 7 is an explanatory view illustrating the movement of an ion in the porous dielectric powder.

That is, natural pumice stone has a certain degree of electric conductivity, in other words, a small resistance component R. In addition, it is presumed that the ions in the air holes (or voids) H, H . . . undergo irregular Brownian motion as shown in FIG. 7.

Therefore, when a negative high voltage of (−)6 KV is applied across the first and second planar electrodes 35 and 36 from the DC high-voltage power source 2, electric discharge occurs between the first and second planar electrodes 35 and 36 and electrons (e⁻) generated by the electric discharge collide with the porous dielectric powder 33. Then, electrons bound in the crystalline particles A, A . . . of the porous dielectric powder 33 are released by the collision energy and electrons and initial positive and negative ions are generated.

The initial ions are converted into nuclear ions through some chemical reactions. After that, the number of electros or ions moving around in the air holes (or voids) increases, and the electric conductivity of the porous dielectric powder 33 increases. Since a large number of air holes (voids) interconnected with each other serve as a cavity, the electrons or ions moves in the air holes (or voids) toward the second planar electrode 36 with vigorous Brownian motion. This is also causes generation of a pulsating voltage with a specific period from the second planar electrode 36.

If the porous dielectric powder 33 is substituted with a metal material with high electric conductivity, the output from the DC high-voltage power source 2 is transmitted by the free electrons of the metal material and outputted from the voltage converter 3 as it is. Although a metal material has a resistance component R, it has no capacitance component C and Brownian motion of electrons does not occur since there is no air hole (or void) in the metal material.

At this time, since the first and second auxiliary electrodes 13 and 14 electrically connected to the first and second planar electrodes 35 and 36 are provided between the first and second planar electrodes 35 and 36 opposed to each other as described above, the first and second auxiliary electrodes 13 and 14 create substantially the same effects as increasing the areas of the first and second planar electrodes 35 and 36 opposed to each other as a whole and as decreasing the distance between the first and second planar electrodes 35 and 36. As a result, the electrostatic capacitance of the voltage converter 3 as a capacitive voltage converter increases as described later.

When the electrostatic capacitance increases, the amplitude of the pulsating voltage to be applied to the discharging electrode 4 for generating negative ions increases and corona discharge occurs more easily. As a result, the negative ion generation efficiency increases.

The discharging electrode 4 for generating negative ions has a first discharging electrode 4a to which a negative high DC voltage of −6 KV from the voltage converter 3 is applied and a second discharging electrode 4b with a ground potential of 0 V, and the first and second discharging electrodes 4a and 4b are connected to the second lead terminal 39 of the voltage converter 3 and a ground potential GND of the high-voltage power source 2 via first and second cables 11 and 12 with prescribed lengths, respectively.

The first and second discharging electrodes 4a and 4b are made, for example, of a conductive stainless steel plate around which a copper sulfate impregnated conductive fabric is wound.

When electric potential treatment is conducted, a part of a human body 5 (a finger is shown in FIG. 1) is pinched by the first and second discharging electrodes 4a and 4b.

Then, negative ions (or electrons e⁻ having negative charge) generated by corona discharge between the first and second discharging electrodes 4a and 4b enter the human body 5 through the skin thereof to reduce the acidic level of blood components or suppress the oxidation of blood components and to enhance immune functions.

That is, when negative ions are introduced into the human body 5, the oxidation-reduction potential in blood or in red blood cells decreases and the pH of blood and red blood cells increases. Also, the blood serum LDL concentration, lipid peroxide concentration and thiobarbituric acid reaction products concentration as indicators of oxidant stress in bodies decrease and 8-OHdG concentration in urine decreases remarkably.

Measurement Example:

To confirm the above effects, negative ions generated by corona discharge were applied directly to a surface of artificial skin as a model of the human body 5 with the electric potential treatment instrument shown in FIG. 1 and the permeability of the negative ions was observed.

(1) Measuring Method:

Pieces of artificial skin (Living Skin Equivalent, product of TOYOBO Co. Ltd.) were attached to both ends of a circular cylindrical glass cell and the cell was filled with 2 cc of normal saline solution.

The second discharging electrode 4b of the device shown in FIG. 1 was fixedly attached to the honey layer side of the artificial skin on one end of the cell, and the first discharging electrode 4a was fixedly attached to the honey layer side of the artificial skin on the other end of the cell.

The device shown in FIG. 1 was operated to apply negative ions to the artificial skin. The oxidation-reduction potential and pH of the normal saline solution in the cell were measured 15 and 30 minutes later (negative ion irradiated group).

In the measurement of the oxidation-reduction potential, the results were corrected to values at a water temperature of 25° C.

The same procedure was repeated except that the device shown in FIG. 1 was not operated (control group).

(2) Measurement Result:

The oxidation-reduction potential and pH of the normal saline solution were 495.3 (value before correction: 289.3) mV and 6.00 in average, respectively, before the irradiation of negative ions. In the negative ion irradiated group, the oxidation-reduction potential was decreased to 446.8 (240.8) mV in average and the pH increased to 6.58 in average after 15 minutes' irradiation of negative ions.

After 30 minutes' irradiation of negative ions, the oxidation-reduction potential decreased to 418.3 (212.3) mV in average and the pH increased to 6.88 in average.

In the control group, the oxidation-reduction potential showed a slight decrease with time and the pH showed a slight increase with time. After 15 minutes, the actual measurement value of the oxidation-reduction potential did not show a significant difference from that of the negative ion irradiated group although it showed a significant decrease. The pH showed a significant change and a significant difference from that of the negative ion irradiated group.

After 30 minutes' irradiation of negative ions, both the oxidation-reduction potential and pH showed significant changes and significant differences from those of the negative ion irradiated group. That is, the oxidation-reduction potential showed a decrease and the pH showed an increase.

(3) Analysis:

Approximately $4\times10^6/cm^3$-air of negative ions are measured in air around the second discharging electrode 4b of the electric potential treatment instrument used in this measurement shown in FIG. 1. When the artificial skin was directly irradiated with the negative ions, a decrease in oxidation-reduction potential and an increase in pH were observed in the normal saline solution on the side of the dermis of the artificial skin. It was therefore proved that negative ions can enter a human body through skin.

The artificial skin (Living Skin Equivalent, product of TOYOBO Co. Ltd.) is a perfect replica model of human skin and has been proved to be close to human skin morphologically and biochemically. This model has two layers: an upper layer of differentiated and layered human epithelial cells and a lower layer of collagen gel in which skin fibro-blast cells are buried. The epidermis has a basal cell layer, a prickle cell layer and a horny layer, and the dermis has no hair root, no sweat gland and no blood vessel but can produce collagen gel and glucosaminoglycan.

It has been traditionally thought that negative ions are taken into a human body mainly through the airways and alveoli but the above results of measurement indicates that permeation of negative ions through skin and mucosa is also important.

Possible routes of entry of negative ions are through epidermal cells epidermis and through gaps between epidermal cells. Another possible route through the skin of a living body is through pores and eccrine glands. It is presumed that the negative ions having entered the living body through skin are taken into blood capillaries and delivered to every part of the body to suppress oxidant stress in and around cells and adjust the pH to an optimum alkaline level.

The mechanism by which the negative ions passed through the artificial skin decreased the oxidation-reduction potential of the normal saline solution and increased the pH of the normal saline solution in this measurement is considered as follows.

Normal saline solution is a 0.9% aqueous solution of NaCl and contains oxygen ($O_2$) dissolved from the atmosphere. The negative ions have extra electrons, and the electrons ($e^-$) react with oxygen in the normal saline solution and hydrogen ions ($H^+$) from the dissociation of water to form water with high reducing property. That is, the following reactions occur:

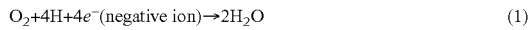

$$O_2 + 4H^+ + 4e^- \text{(negative ion)} \rightarrow 2H_2O \quad (1)$$

$$H^+ + e^- \text{(negative ion)} \rightarrow H(H_2) \quad (2)$$

In other words, the electrons ($e^-$) of the negative ions decrease the oxidation-reduction potential of the normal saline solution, and a decrease of hydrogen ions concentration causes an increase in pH. It is thought that the reaction (2) occurs mainly when negative ions taken into a living body through the lung and blood capillaries in skin are delivered to every part of the body.

That is, it is thought that the electrons of the negative ions are attached to hydrogen ions in blood and cause reduction reactions in the body; for example, the electrons are taken into oxidized vitamins and amino acids (peptides) to convert them into reduced vitamins and amino acids, or trivalent iron ions ($Fe^{3+}$) receive electrons from the negative ions and transform into bivalent iron ions ($Fe^{2+}$). Especially, it is thought that coenzymes such as $NAD^+$ and $NADP^+$ as electron recipients in cells receive negative ions and cause changes in the oxidation-reduction potential in the living body.

The decrease in blood serum LDL and 8-OHdG concentration in urine as indicators of oxidant stress in a living body upon direct irradiation of a human body with negative ions is thought to be caused by the reducing property of the negative ions.

The present invention may be embodied in various forms for example as illustrated in FIGS. 8 to 23. In FIGS. 1-23, the same reference numerals designate similar or substantially equivalent component parts.

Modification:

In the first embodiment, the first and second auxiliary electrodes 13 and 14 are located at the bottom of the case body 31 for easy installation.

Figure 8:
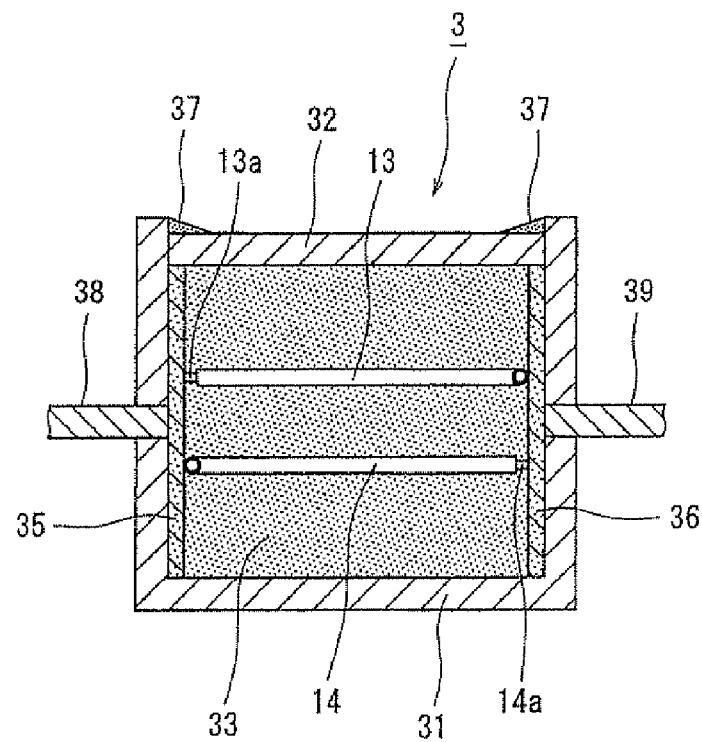
FIG. 8 is a cross-sectional view illustrating the configuration of a modification of the voltage converter for the first embodiment.

The first and second auxiliary electrodes 13 and 14 may be, however, arranged at a vertical intermediate position in the case body 31 with a prescribed distance therebetween as shown in FIG. 8.

When the first and second auxiliary electrodes 13 and 14 are arranged at a vertical intermediate position in the space between the first and second planar electrodes 35 and 36, since the dielectric charge is uniformly distributed vertically in the porous dielectric powder (dielectric material) 33 between the first and second planar electrodes 35 and 36, the electrostatic capacitance can be further increased.

In this case, the porous dielectric powder 33 is first filled in the case body 31 up to a first level and tamped down tightly.

Next, the second auxiliary electrode 14 is placed on the porous dielectric powder 33 horizontally with the both ends of the cable core 14a connected to the second planar electrode 36.

The porous dielectric powder 33 is filled in the case body 31 up to a second level and tamped down tightly to fix the second auxiliary electrode 14 in position.

The first auxiliary electrode 13 is placed on the porous dielectric powder 33 horizontally with the both ends of the cable core 13a connected to the first planar electrode 35.

Then, the porous dielectric powder 33 is filled in the case body 31 up to a third level (final level) and tamped down tightly. Finally, the cap 32 is fitted to the case body 31 and fixed as shown in FIG. 8.

Second Embodiment

In the first embodiment, the voltage converter 3 according to the present invention is applied to an electric potential treatment instrument for introducing negative ions into human body through skin.

Figure 9:
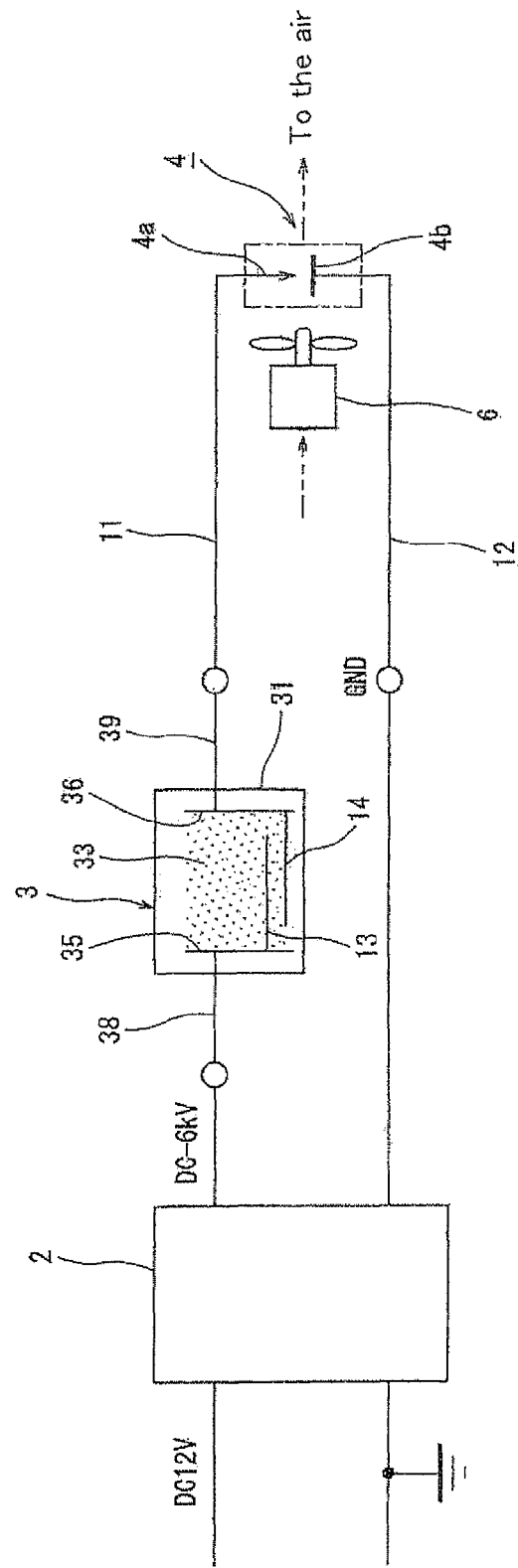
FIG. 9 is a block diagram illustrating the configuration of a negative ion generating device for releasing negative ions into air according to a second embodiment of the present invention to which the voltage converter of the present invention is applied.

In the second embodiment, the voltage converter 3 is applied to a negative ion generating device for introducing negative ions generated at a discharging electrode 4 into a human body through airway with a blowing means 6 such as a blowing fan as shown in FIG. 9.

The other configuration is basically the same as the first embodiment.

The negative ion generating device according to this embodiment can be used on its own and can be also incorporated in various devices such as air purification systems and air conditioners.

In such a negative ion generating device (discharging electrode 4 for generating negative ions), the voltage converter 3 constituted as described above can produce a good effect and improve the negative ions generation efficiency.

Third Embodiment

Figure 10:
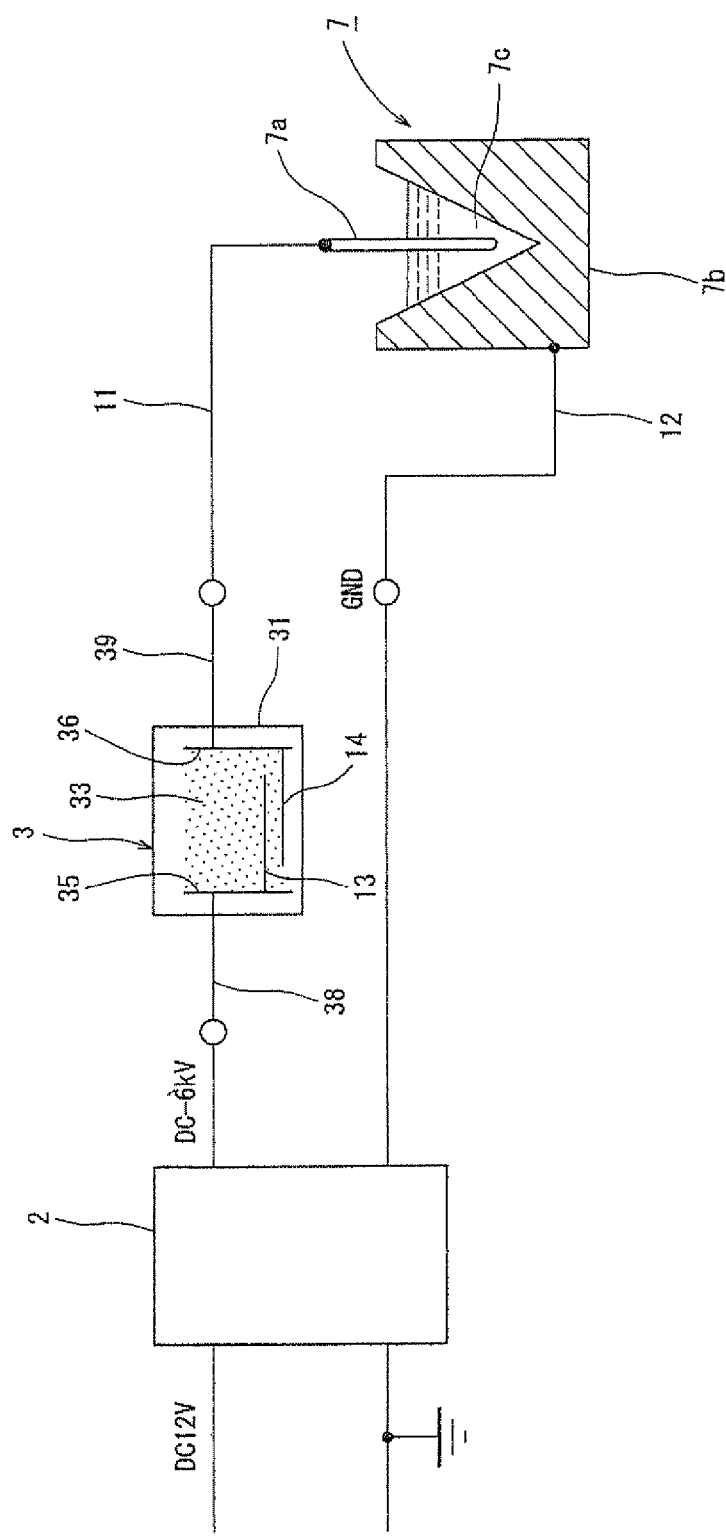
FIG. 10 is a block diagram illustrating the configuration of a negative ion generating device for producing negative ion water according to a third embodiment of the present invention to which the voltage converter of the present invention is applied.

In the third embodiment, the voltage converter 3 is applied to a negative ion generating device for producing negative ion water as shown in FIG. 10.

The other configuration is basically the same as the first embodiment.

The negative ion generating device for producing negative ion water has a second discharging electrode 7b on the ground side forming a water reservoir 7c with a V-shaped cross-section, and a needle-like first discharging electrode 7a on the negative side located in the water reservoir 7c and opposed to the second discharging electrode 7b.

The water (tap water, for example) in the water reservoir 7c is converted into negative ion-reduced water with a low ORP by the water reduction effect of the negative ions generated by corona discharge between the first and second discharging electrodes 7a and 7b. In such a negative ion generating device (discharging section 7 for generating negative ions) for producing negative ion water, the voltage converter 3 constituted as described above can produce a good effect and improve negative ions generation efficiency.

EXAMPLE

FIGS. 11 to 14 show the configuration of a specific embodiment of the voltage converter common to the first to third embodiments of the present invention.

As shown in FIG. 11 to FIG. 14, the voltage converter 3 has a nonconductive case having a case body 31 in the shape of a square box with a bottom and an upper opening made of a synthetic resin such as ABS, and first and second caps 32A and 32B made of a synthetic resin such as ABS and fitted in the upper opening of the case body 31; first and second planar electrodes 35 and 36 of a conductive stainless steel provided on inner opposite sides of the nonconductive case; first and second U-shaped auxiliary electrodes 13 and 14 electrically connected to the electrode surfaces of the first and second planar electrodes 35 and 36, respectively; and a porous dielectric powder 33 as a dielectric material such as natural pumice stone powder with an outside diameter of 1 to 200 μm and a water content of 2.5% to 4.0% uniformly filled in the cubic space in the nonconductive case. The porous dielectric powder 33 has been filled in the case body 31 under strict moisture control and the case body 31 has been sealed hermetically by the caps 32A and 32B so that the humidity in the case body 31 can be maintained at a desired level (62%).

The first and second auxiliary electrodes 13 and 14 are made of insulating covered stranded cables (high-voltage cables) having conductive cable cores 13a and 14a of tin-plated copper (made by twining a multiplicity of tin-plated copper wires), insulating tubes 13b and 14b of an insulating material such as ilex, and exterior tubes 13c and 14c of an insulating material such as vinyl chloride, respectively, as shown in FIG. 3 and FIG. 4.

Figure 13:
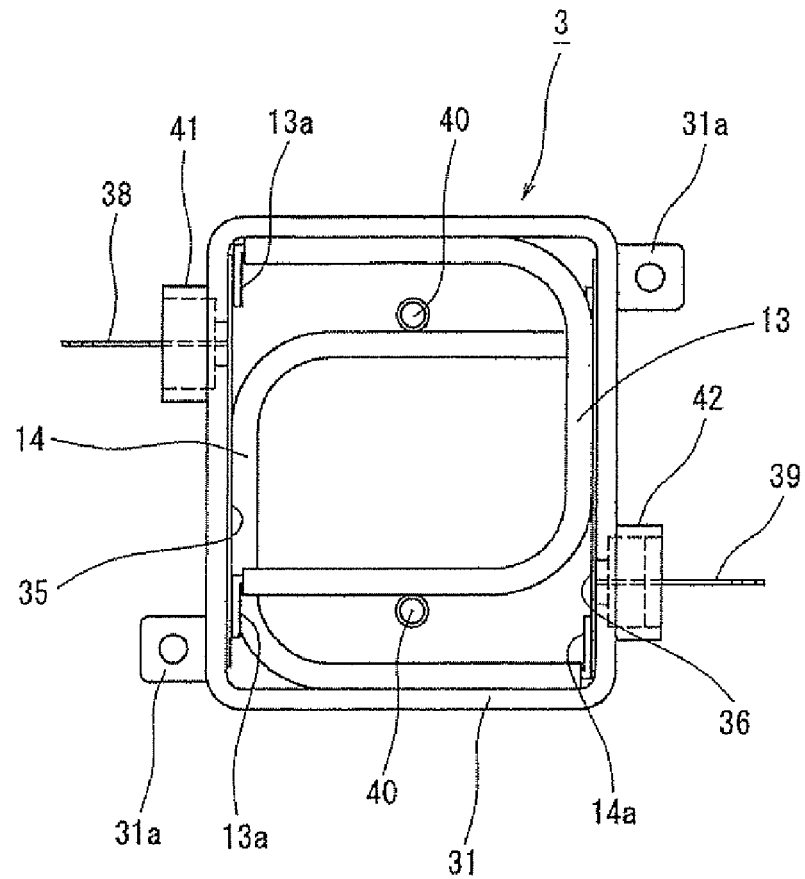
FIG. 13 is a plan view illustrating the configuration of the voltage converter before being sealed.
Figure 14:
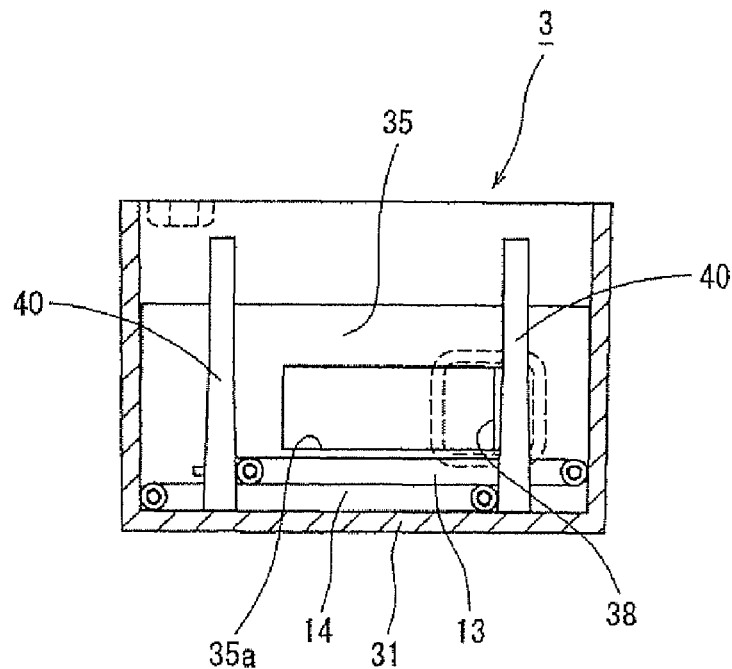
FIG. 14 is a central vertical cross-sectional view illustrating the constitution of a voltage converter before being sealed.

The first and second auxiliary electrodes 13 and 14 are located at the bottom of the case body and stacked in part as shown in FIGS. 13 and 14.

In the case body 31, first and second poles 40 and 40 extend upward from the bottom. The first and second auxiliary electrodes 13 and 14 are held in proper shape and position by the first and second poles 40 and 40 as shown in FIG. 13.

The both ends of the cable cores 13a and 14a protrude from the both ends of the first and second auxiliary electrodes 13 and 14 and bent at a right angle in the same direction.

Since the first and second auxiliary electrodes 13 and 14 are supported by the first and second poles 40 and 40 and arranged so as to be pressed against the first and second planar electrodes 35 and 36 as shown in FIG. 13, the first and second auxiliary electrodes 13 and 14 are maintained in electrical connection with the first and second planar electrodes 35 and 36, respectively, without any connecting means such as solder.

The first and second auxiliary electrodes 13 and 14 arranged between the first and second planar electrodes 35 and 36 opposed to each other with the both ends of the cable cores 13a and 14b electrically connected to the first and second planar electrodes 35 and 36, respectively, as described above, can create substantially the same effects as increasing the areas of the first and second planar electrodes 35 and 36 opposed to each other as a whole and as decreasing the distance between the first and second planar electrodes 35 and 36. As a result, the electrostatic capacitance of the voltage converter 3 as a capacitive voltage converter increases effectively as described later.

When the electrostatic capacitance increases, the amplitude of the pulsating voltage applied to the discharging electrode 4 or 7 increases and corona discharge occurs more easily.

As a result, negative ion generation efficiency increases.

In addition, since the first and second auxiliary electrodes are stacked in part, the auxiliary electrodes 13 and 14 are distributed generally uniformly in the space between the first and second planar electrodes and the electrostatic capacitance of the voltage converter 3 can be increased more effectively.

In addition, since the first and second auxiliary electrodes 13 and 14 are made of insulating covered cables, the first and second auxiliary electrodes 13 and 14 may be placed in contact with each other. Therefore, the first and second auxiliary electrodes 13 and 14 can be installed easily.

Moreover, since the first and second auxiliary electrodes 13 and 14 are located at the bottom of the case body 31 as shown in FIG. 14, when the porous dielectric powder 33 is placed over the first and second auxiliary electrodes 13 and 14 and tamped down tightly, the first and second auxiliary electrodes 13 and 14 can be fixed easily and reliably in the case body 31 with their electrical connection to the planar electrodes 35 and 36 maintained.

Therefore, the first and second auxiliary electrodes 13 and 14 require any attaching or fastening means and thus can be produced easily.

The first and second planar electrodes 35 and 36 have center portions 35a and 36a (36a is not shown) cut in a rectangular shape and bent outward at a right angle to form first and second lead terminals 38 and 39 protruding a prescribed length outward through the front and rear walls of the case body 31 and connected to the output terminal of the DC high-voltage power source 2 and the input terminal of the first discharging electrode 4a, respectively.

At the openings of the case body 31 through which the first and second lead terminals 38 and 39 protrude outward, sealant filled parts 41 and 42 are formed. The sealant filled parts 41 and 42 are filled with a sealant to ensure good seal and mechanical fixation.

When the first and second lead terminals 38 and 39 are formed by cutting and bending parts of the first and second planar electrodes 35 and 36, there is no need for connection between the first and second lead terminals 38 and 39 and the first and second planar electrodes 35 and 36. Therefore, the voltage converter 3 can be simple in structure and can be produced easily at low cost.

Also, troubles such as poor connection at joints can be prevented and the reliability of the products can be improved.

The case body 31 is closed by the first and second caps 32A and 32B in the upper opening thereof and sealed by an adhesive 37 filled in the gap between the first and second caps 32A and 32B.

Figure 11:
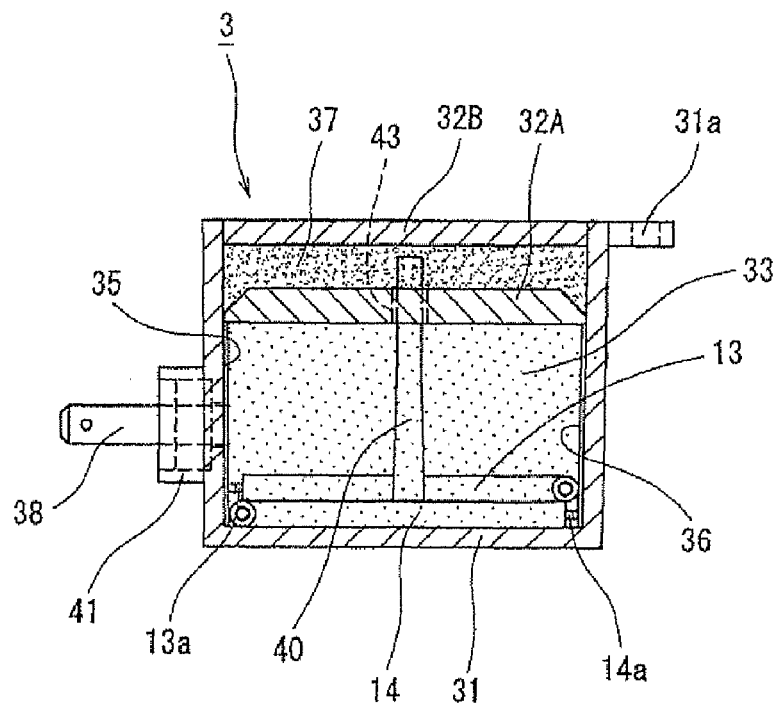
FIG. 11 is a central vertical cross-sectional view illustrating the configuration of a voltage converter for a negative ion generating device for the embodiments of the present invention.

As shown in FIG. 11, the first cap 32A with a prescribed thickness has a lower side with the same shape and area as the upper opening of the case body 31 and an outer periphery tapered upward. The first cap 32A also has holes 43 and 43 for receiving the first and second poles 40 and 40 at both sides in the lateral direction. After the first and second auxiliary electrodes 13 and 14 has been placed and the porous dielectric powder 33 has been filled in the case body 31 up to a level slightly higher than the level of the first cap 32A shown in FIG. 11, the first cap 32A is placed on the porous dielectric powder 33 using the first and second poles 40 and 40 as guides and pressed downward by a pressing means. The porous dielectric powder 33 is pressed tightly to the extent that it cannot be moved even if vibrated. The first and second auxiliary electrodes 13 and 14 at the bottom of the case body 31 are fixed reliably with the both ends of the cable cores 13a and 14a in pressure contact with the first and second planar electrodes 35 and 36, respectively.

To keep this state more reliably, an elastic adhesive 37 such as a silicon-modified polymer adhesive is placed on the first caps 32A in a press-fitted and cured to seal the first caps 32A.

Then, the second cap 32B as an external cap is placed on the adhesive 37 and fixed.

Figure 12:
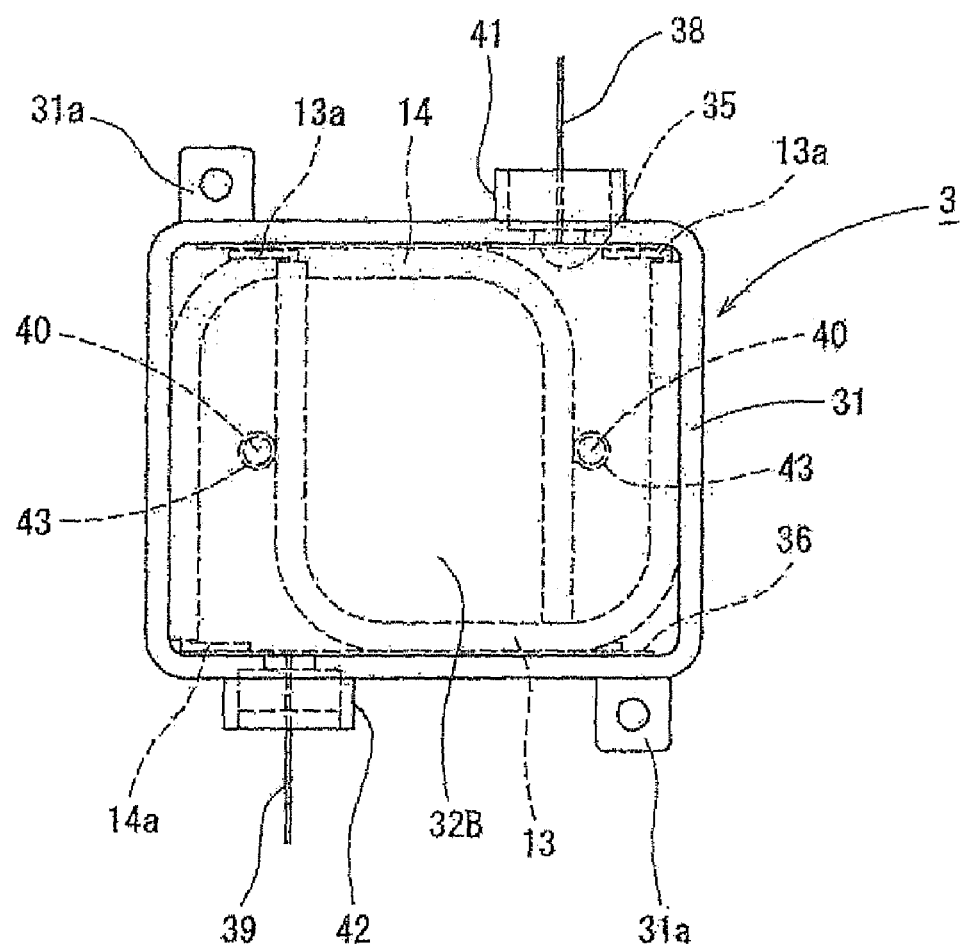
FIG. 12 is a plan view illustrating the configuration of the voltage converter.

The voltage converter 3 shown in FIG. 11 and FIG. 12 is thereby assembled.

Designated as 31a in FIG. 11 to FIG. 14 is a fastener for use in fixing the negative ion generating device to a base or case.

Figure 15:
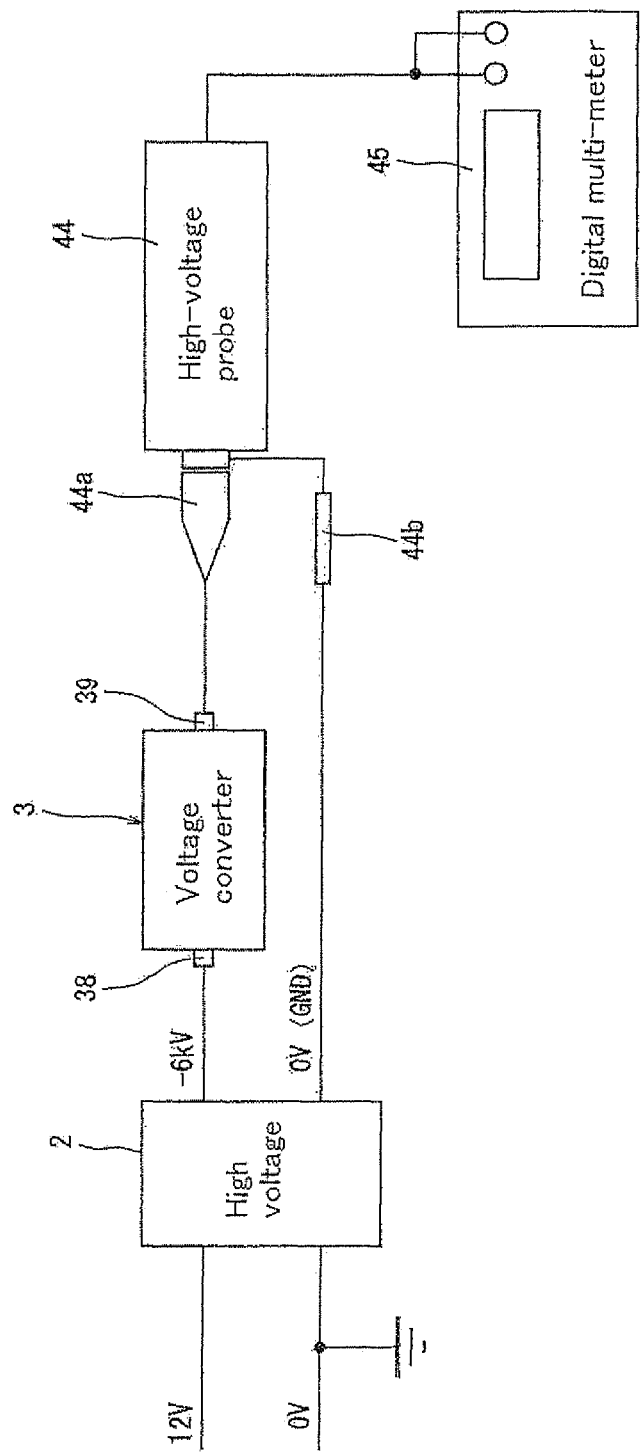
FIG. 15 is a circuit diagram of a measurement system used to measure the waveform of output voltage from the voltage converter shown in FIG. 11 to FIG. 14.

Measurement Result:

(1) Measurement of Voltage Waveform:

The waveform of the output voltage from the voltage converter as shown in FIG. 11 to FIG. 14 was observed with a digital multi-meter (digital oscilloscope) 45 as shown in FIG. 15 in the following two cases: (A) the first and second auxiliary electrodes 13 and 14 were provided, and (B) the first and second auxiliary electrodes 13 and 14 were not provided. The voltage input terminals of the digital multi-meter 45 were connected to the second lead terminal 39 of the voltage converter 3 shown in FIG. 11 to FIG. 14 and the ground terminal (0 V) of the DC high-voltage power source unit 2 via coupling terminals 44a and 44b of a high-voltage probe 44, respectively.

Figure 16B:
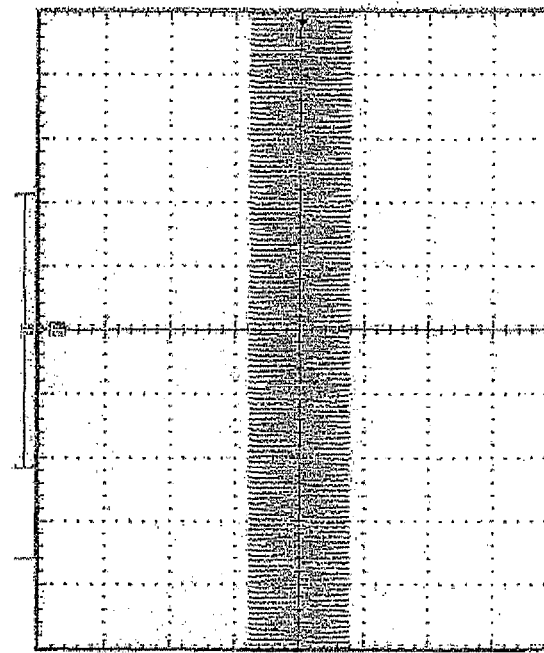
FIGS. 16(*a*) and 16(*b*) are waveform charts showing the results of measurement of the waveform of output voltage from the voltage converter shown in FIG. 11 to FIG. 14 at a first (minimum) scale, FIG. 16(*a*) showing the waveform in the case where the first and second auxiliary electrodes were provided, and FIG. 16 (*b*) showing the waveform in the case where the first and second auxiliary electrodes were not provided.
Figure 16A:
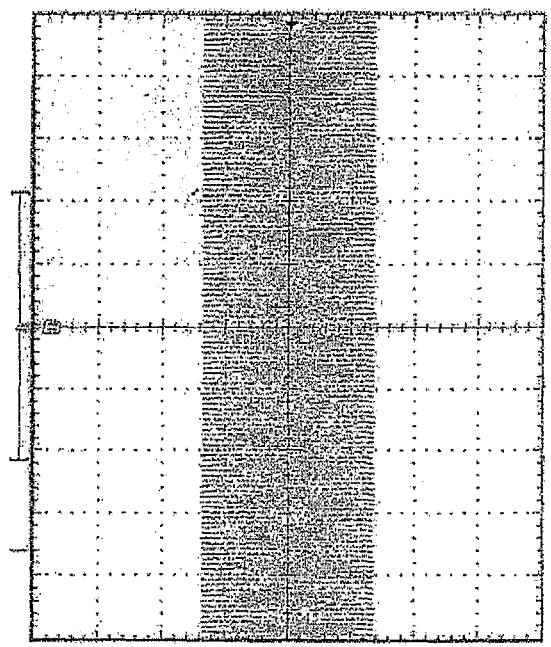
Figure 17B:
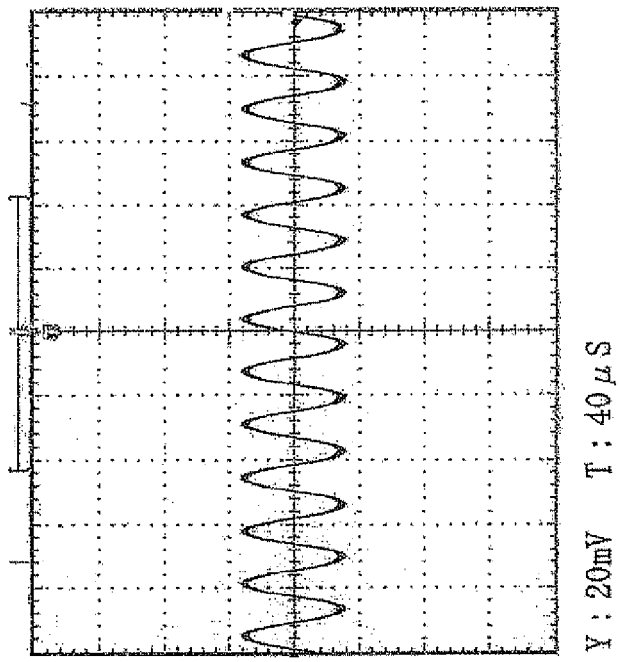
FIGS. 17(*a*) and 17(*b*) are waveform charts showing the results of measurement of the waveform of output voltage from the voltage converter shown in FIG. 11 to FIG. 14 at a second (intermediate) scale, FIG. 17 (*a*) showing the waveform in the case where the first and second auxiliary electrodes were provided, and FIG. 17(*b*) shows the waveform in the case where the first and second auxiliary electrodes were not provided.
Figure 17A:
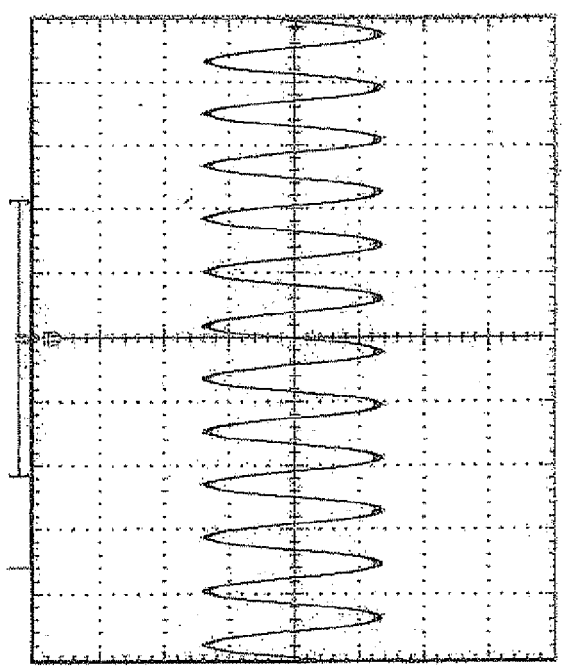
Figure 18A:
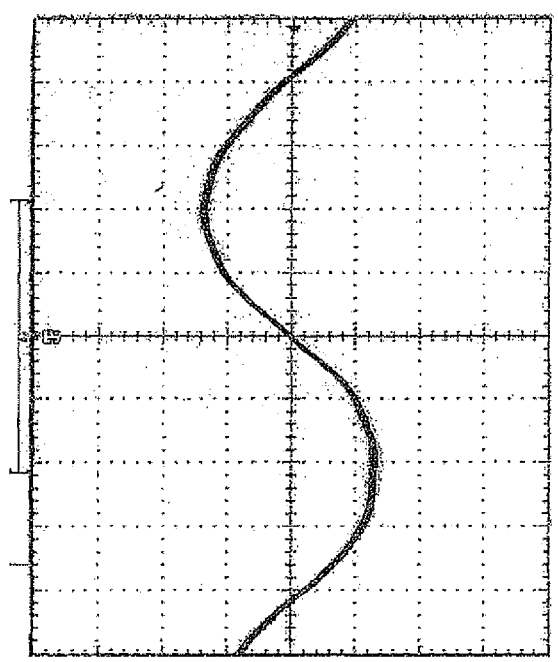
FIGS. 18(*a*) and 18(*b*) are waveform charts showing the results of measurement of the waveform of output voltage from the voltage converter shown in FIG. 11 to FIG. 14 at a third (maximum) scale, FIG. 18 (*a*) showing the waveform in the case where the first and second auxiliary electrodes were provided, and FIG. 18 (*b*) showing the waveform in the case where the first and second auxiliary electrodes were not provided.
Figure 18B:
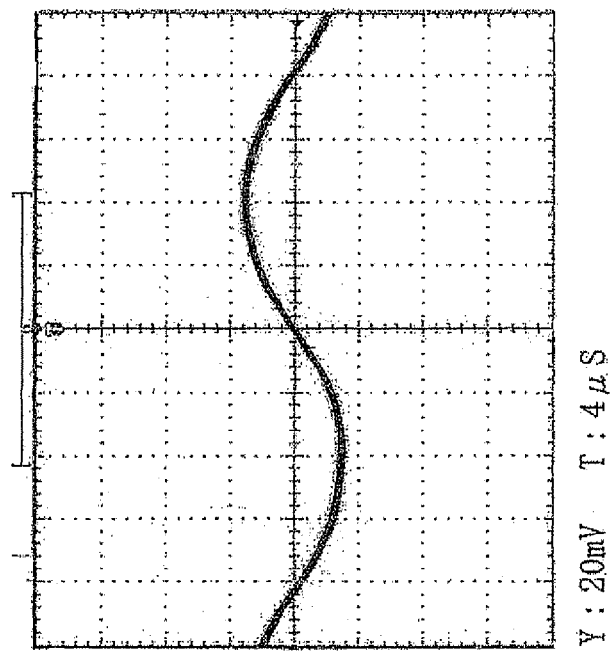

The voltage waveform as the result of measurement is shown in three different scales (minimum, intermediate, and maximum) in FIGS. 16(a), 16(b), 17(a), 17(b), 18(a) and 18(b). In FIGS. 16(a), 17(a) and 18(a) show the results of the case (A), and FIGS. 16(b), 17(b) and 18(b) show the result of the case (B).

As is clear from the measurement result, the amplitude (the size from peak to peak) of the output voltage in the case (A) was much larger than that in the case (B).

Figure 19:
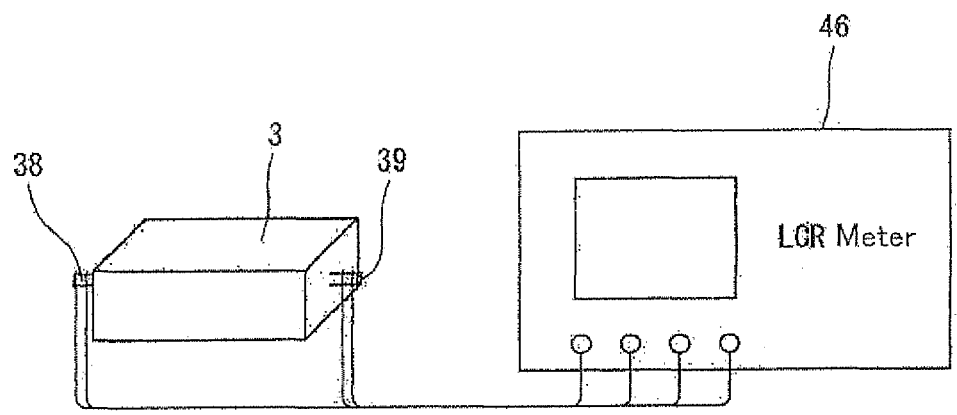
FIG. 19 illustrates a measurement system used to measure the electrostatic capacitance of the voltage converter.

(2) Measurement of Electrostatic Capacitance:

The electrostatic capacitance of the voltage converter 3 as shown in FIG. 11 to FIG. 14 was measured with an LCR meter (LCR tester) 46 shown in FIG. 19 in the following two cases for comparison: (a) the first and second auxiliary electrodes 13 and 14 were provided, and (b) the first and second auxiliary electrodes 13 and 14 were not provided.

The results are summarized in Table 1.

TABLE 1

|  |  | Case (a) | | | Case (b) | | |
|---|---|---|---|---|---|---|---|
|  |  | Type A | Type B | AVE | Type C | Type D | AVE |
| AC | Electrostatic capacitance (PF) | 11.37 | 11.18 | 11.28 | 3.19 | 3.19 | 3.19 |
|  | Resistance (MΩ) | 2.41 | 2.41 | 2.41 | 3.06 | 3.15 | 3.11 |
|  | Pk-Pk voltage (V) | 50.4 | 56.4 | 53.4 | 31.6 | 30.4 | 31 |
| DC | High-voltage supply voltage (kV) | 6 | 6 | 6 | 6 | 6 | 6 |
|  | Voltage after conversion (kV) | 5.901 | 5.907 | 5.904 | 5.909 | 5.907 | 5.908 |

As is clear from the measurement result, the electrostatic capacitance in the case (a) was much greater than that in the case (b). Also, the resistance was smaller and the peak widths of the output voltage were much greater.

The above results indicate that corona discharge can be generated at the discharging electrode 4 or 7 in the above embodiments more effectively than in conventional devices and the negative ion generation efficiency can be improved effectively.

Although the voltage converter according to the above embodiments has U-shaped, first and second auxiliary electrodes electrically coupled to respective planar electrodes, the number, arrangement and shape of the auxiliary electrodes are not specifically limited to those of the above embodiments. Thus, the number of the auxiliary electrode may be only one. When a plurality of auxiliary electrodes are used, all of them can be connected only one of the two planar electrodes. It is preferable, however, that the plural auxiliary electrodes be nearly symmetrically arranged or nearly evenly distributed for reasons of ensuring stable operation.

Further, the auxiliary electrode may be in the form of a straight or curved rod, plate, coil or any other desired shape. Some examples of the arrangement and configuration of the auxiliary electrodes are shown in FIGS. 20 to 23.

Figure 20:
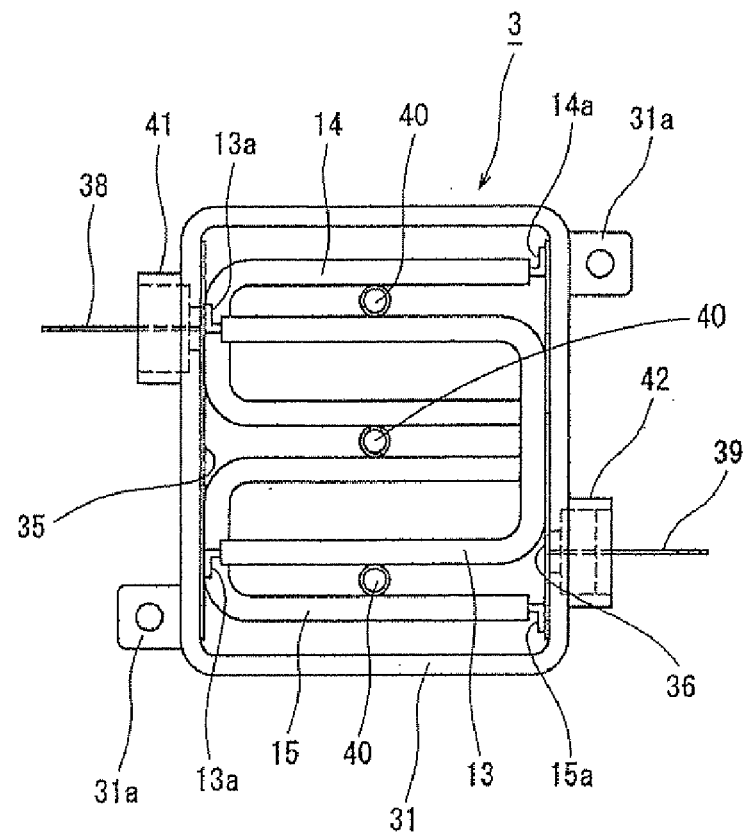
FIG. 20 is a plan view, similar to FIG. 13, illustrating the configuration of a voltage converter as a modification of the voltage converter for the embodiments of the present invention.
Figure 21:
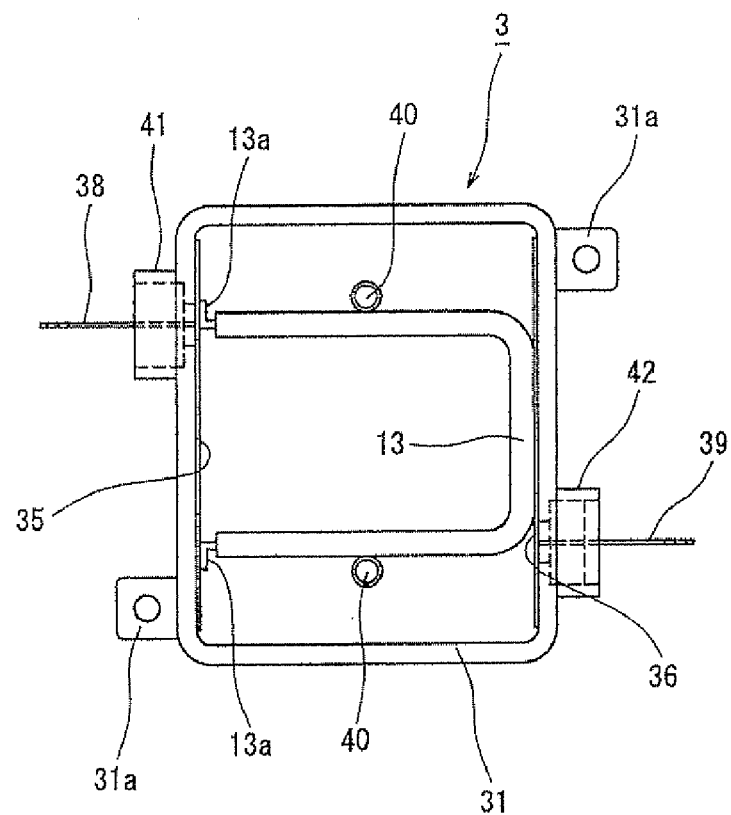
FIG. 21 is a plan view, similar to FIG. 13, illustrating another example of the configuration of a voltage converter as a modification of the voltage converter for the embodiments of the present invention.
Figure 22:
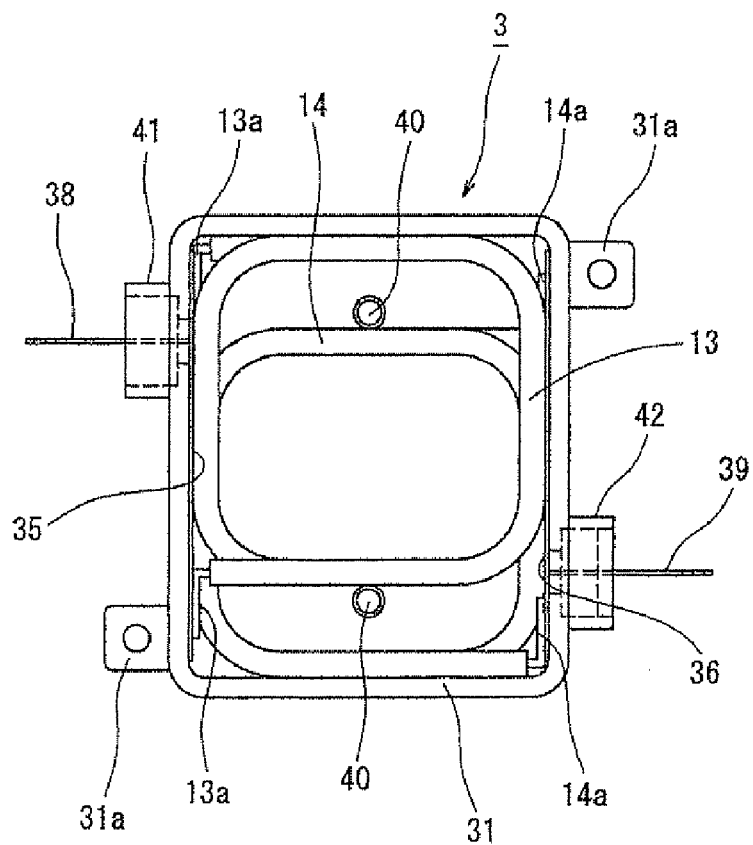
FIG. 22 is a plan view, similar to FIG. 13, illustrating a further example of the configuration of a voltage converter as a modification of the voltage converter for the embodiments of the present invention.
Figure 23:
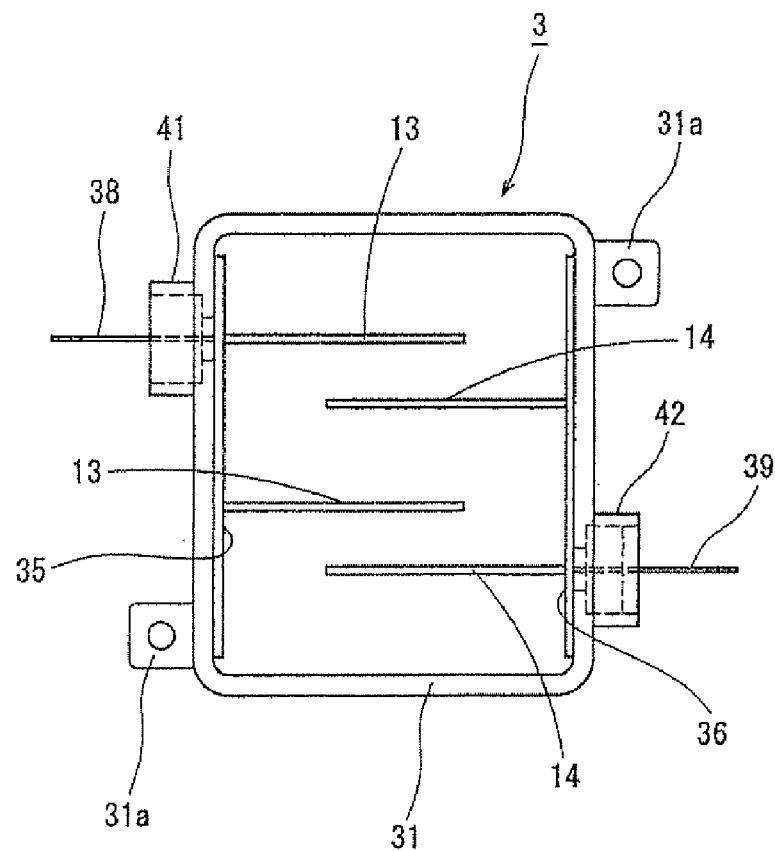
FIG. 23 is a plan view, similar to FIG. 13, illustrating a still further example of the configuration of a voltage converter as a modification of the voltage converter for the embodiments of the present invention.

In the embodiment shown in FIG. 20, one U-shaped auxiliary electrode 13 is connected to a first planer electrode 35 at its end 13a, while two U-shaped auxiliary electrodes 14 and 15 are connected to a second planer electrode 36 at their ends 14a and 15a. In the embodiment shown in FIG. 21, the voltage converter 3 has only one U-shaped auxiliary electrode 13 connected to one planar electrode 35. In the embodiment shown in FIG. 22, two coiled auxiliary electrodes 13 and 14 are connected to first and second planer electrodes 35 and 36, respectively. The auxiliary electrodes in FIGS. 20 to 22 are each made of an insulating covered stranded cable. In the embodiment shown in FIG. 23, two parallel auxiliary electrodes 13 extend from the first planer electrode 35 in the direction normal thereto. Also, two parallel auxiliary electrodes 14 extend from the second planer electrode 36 in the direction normal thereto. The four auxiliary electrodes 13 and 14, which are bare electric wires, are symmetrically arranged.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

This application claims priority of Japanese Patent Application No. 2005-222871, filed Aug. 1, 2005, disclosures of which, inclusive of the specification, claims and drawings, are hereby incorporated by reference herein.

The invention claimed is:

1. A voltage converter, comprising:
 a sealed case;
 a pair of first and second planar electrodes located within said sealed case and opposed to each other with a gap therebetween;
 a pack of porous dielectric powder filled in said gap; and
 a first auxiliary electrode electrically connected to said first planar electrode and having a portion extending through said pack of porous dielectric powder toward said second planar electrode;
 whereby when a DC high voltage is applied to one of said first and second planar electrodes, a DC source voltage containing a specific pulsating component is outputted from the other one of said first and second planar electrodes.

2. A voltage converter according to claim 1, wherein said first auxiliary electrode is made of an insulating covered cable.

3. A voltage converter according to claim 1, further comprising a second auxiliary electrode electrically connected to said second planar electrode and having a portion extending through said pack of porous dielectric powder toward said first planar electrode.

4. A voltage converter according to claim 3, wherein said first and second planer electrodes are disposed in parallel with each other, wherein each of said first and second auxiliary electrodes is U shaped with its two legs extending normal to said planar electrodes and electrically connected to the corresponding planar electrode, and wherein said first and second auxiliary electrodes are stacked in part.

5. A voltage converter according to claim 4, wherein each of said first and second auxiliary electrodes is made of an insulating covered cable.

6. A voltage converter according to claim 5, wherein said first and second auxiliary electrodes are located at the bottom of said sealed case.

7. A negative ion generating device, comprising:

a voltage converter according to claim 1, a DC high-voltage power source electrically connected to said first planar electrode; and a discharging electrode having an input connected to said DC source voltage which contains a specific pulsating component and which is outputted from said voltage converter.

8. A negative ion generating device according to claim 7, and being an electric potential treatment instrument for applying negative ions to a living body, a negative ion generating device for emitting negative ions into the air, or a negative ion water producing device for producing negative ion water.

9. A voltage converter according to claim 1, further comprising a second auxiliary electrode electrically connected to said second planar electrode and having a portion extending through said pack of porous dielectric powder toward said first planar electrode.

10. A voltage converter according to claim 9, wherein said first and second planer electrodes are disposed in parallel with each other, wherein each of said first and second auxiliary electrodes is U shaped with its two legs extending normal to said planar electrodes and electrically connected to the corresponding planar electrode, and wherein said first and second auxiliary electrodes are stacked in part.

11. A voltage converter according to claim 10, wherein each of said first and second auxiliary electrodes is made of an insulating covered cable.

12. A voltage converter according to claim 11, wherein said first and second auxiliary electrodes are located at the bottom of said sealed case.

* * * * *

UNITED STATES PATENT AND TRADEMARK OFFICE
CERTIFICATE OF CORRECTION

| | | |
|---|---|---|
| PATENT NO. | : 7,821,764 B2 | Page 1 of 1 |
| APPLICATION NO. | : 11/989592 | |
| DATED | : October 26, 2010 | |
| INVENTOR(S) | : Noboru Horiguchi | |

It is certified that error appears in the above-identified patent and that said Letters Patent is hereby corrected as shown below:

Column 17, line 7 (claim 3, line 1) delete "1" and insert --2--.

Signed and Sealed this
Twenty-eighth Day of December, 2010

David J. Kappos
*Director of the United States Patent and Trademark Office*